United States Patent [19]

Brennan

[11] Patent Number: 4,994,084
[45] Date of Patent: Feb. 19, 1991

[54] RECONSTRUCTIVE SURGERY METHOD AND IMPLANT

[76] Inventor: H. George Brennan, 1137 Granville, Newport Beach, Calif. 92660

[21] Appl. No.: 370,453

[22] Filed: Jun. 23, 1989

[51] Int. Cl.$^5$ .............................................. A61F 2/02
[52] U.S. Cl. ...................................... 623/11; 128/898
[58] Field of Search ................ 604/48, 49; 623/11–15, 623/66; 600/36; 128/897, 898, 156; 606/196

[56] References Cited

U.S. PATENT DOCUMENTS

| 3,654,914 | 4/1972 | Franklyn | 128/898 |
| 3,988,782 | 11/1976 | Dardik | 606/229 |
| 4,344,191 | 8/1982 | Wagner | 623/16 |
| 4,643,715 | 2/1987 | Isono et al. | 623/11 |
| 4,756,862 | 7/1988 | Spector et al. | 623/11 |
| 4,770,664 | 9/1988 | Gogolewski | 623/15 |
| 4,772,285 | 9/1988 | Ksander et al. | 128/DIG. 8 |
| 4,889,744 | 12/1989 | Quaid | 128/DIG. 21 |
| 4,938,234 | 7/1990 | Capriotti | 128/898 |

FOREIGN PATENT DOCUMENTS

| 0520978 | 7/1976 | U.S.S.R. | 128/898 |
| 0856443 | 8/1981 | U.S.S.R. | 128/898 |
| 0878266 | 11/1981 | U.S.S.R. | 128/898 |

OTHER PUBLICATIONS

"Instructions for use", brochure for TUTOPLAST ®, Dura Pfrimmer, Pfrimmer-Viggo.
Brochure for PROPLAST ®, Block, 1981, Dow Corning, 3 pages.
Brochure for PROPLAST ®, Sheeting, 1978, Dow Corning, 1 page.
Brochure for Custom Implant Model Kit, 1981, Dow Corning, 2 pages.
Brochure for HISTOACRYL ®, Blue Tissue Adhesive, B. Braun Melsungen AG, 4 pages.

*Primary Examiner*—Stephen C. Pellegrino
*Assistant Examiner*—Sharon Rose
*Attorney, Agent, or Firm*—Knobbe, Martens, Olson & Bear

[57] ABSTRACT

A homograft implant is made from prepackaged, processed homograft material. The homograft material is taken in its purchased dehydrated form and cut into strips of varying shapes and sized. The strips are then adhesively secured together in a laminar manner by a tissue adhesive to form the desired shape and density of the implant. Once the implant has been made, it may then be surgically implanted in a desired location, immediately beneath the patient's dermis so as to alter the exterior appearance of the patient at the implant site. Since the implant is formed of dehydrated homograft material, endogenous tissue readily attaches to the implant after a short period of time, so that the implant becomes integral with the body.

9 Claims, 1 Drawing Sheet

RECONSTRUCTIVE SURGERY METHOD AND IMPLANT

BACKGROUND OF THE INVENTION

The present invention relates generally to the field of cosmetic and reconstructive surgery. More specifically, the present invention is directed toward a homograft implant and method of making and using the same.

Reconstructive and cosmetic surgery has become quite common in recent years. Many people, dissatisfied with their appearance, have turned to cosmetic surgeons to make them more attractive. For cosmetic surgery of the reconstructive type, wherein it is sought to change the underlying bony structure, such as in the nose, a procedure known as grafting is commonly used. In general, grafting entails the implantation of skin or other tissue, from a different site or source, to replace or repair damaged or undesirable bodily structures. If the tissue is removed from one area of the patient's body and implanted elsewhere, the procedure is known as an autograft.

For the nasal area, autograft tissue is usually in the form of cartilage, taken from an area of the nasal septum or from the ear. Not uncommonly, a single layer of cartilage may be sufficient to fill the desired area. If, however, a single layer is insufficient, the cartilage may be carved, and built up to the desired thickness by suturing layers of cartilage tissue together. A major disadvantage of an autograft procedure is that it requires more than one surgical operation. In addition, if the cartilage is taken from the ear, it is substantially thicker than that in the nose. Thus, additional carving must be done to the cartilage prior to implantation. Further, the cartilage in the ear or other area from which it was removed does not regenerate itself. The implant also does not regenerate itself. Moreover, besides the difficulty of working with human cartilage, the sculpted autograph formed from the cartilage may become warped over a period of time, necessitating revision surgery. However, because the tissue is autologous, connective tissue cells will gradually form new intercellular substances which attach the graft in place.

As an alternative, many synthetic materials have been proposed for surgical implantation. These synthetic materials come in various sizes and thicknesses, and may be readily formed into the desired shape. While the synthetic material is readily available and negates the need for multiple operations, connective tissue does not readily attach to the material. This is due to the fact that many of the synthetic materials suitable for use in reconstructive surgery are non-porous or semi-porous and thus cannot become integral with the body. Thus, over a period of time, the body begins to reject the implant and the implanted part is extruded.

Accordingly, there is a need for a reconstructive surgical implant which alleviates the above-mentioned problems.

SUMMARY OF THE INVENTION

Briefly, the present invention provides an homograft implantation device for use in reconstructive surgery. The term homograft refers to implant tissue taken from the same species, in this case, human. The tissue can be human dura mater, fascia, which is the lining of the muscles, or any other collagen matrix tissue. Preferably, dura mater tissue, which is the lining of the brain, is used. The implant tissue is commercially available, processed and prepackaged in small, flat blocks, approximately 0.6 mm thick, and having varying planar dimensions.

Preferably, when it is desired to fill a void in the patient, for example in the nasal bridge, the tissue is cut into strips, of varying sizes. The strips of tissue are then laminated together in several layers using tissue glue to form the desired shape and density of the implant. When the laminar implant is ready for insertion, a small incision is made inside the nasal cavity. Using forceps, the implant is guided into the depressed area, between the nasal cartilage and the dermis. Once inserted, the implant can be manipulated through the epidermis, to ensure proper placement. It is noteworthy that the implant is dehydrated and is thus sufficiently stiff to facilitate ease of implantation, yet sufficiently pliable so as to be biased toward the nasal cartilage by the existing dermis. Advantageously, endogenous tissue readily attaches to the homograft implant so that, after a short period of time, the implant is integral with the body.

Further objects, features and other advantages of the present invention will become apparent from the ensuing detailed description, considered together with the appended drawings.

DETAILED DESCRIPTION OF THE PREFERRED EMBODIMENT

Figure 1:
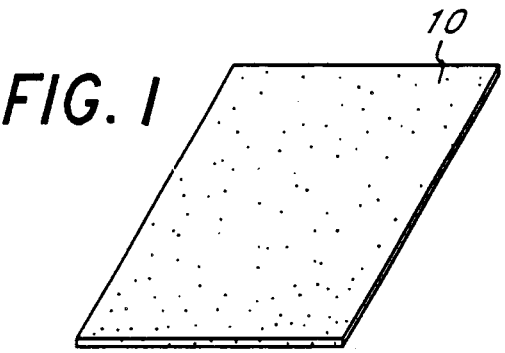
FIG. 1 is a perspective view of a piece of thin tissue homograft.

Referring now to the drawings in detail, wherein like reference numerals designate like elements throughout the several views thereof, there is shown generally at 10 in FIG. 1, a piece of thin tissue homograft, suitable for use with the present invention. Preferably, the homograft comprises processed human tissue having a collagen matrix, such as dura mater or fascia muscle lining. By way of example, Tutoplast ® tissue, comprising dehydrated dura mater, which is commercially available from and manufactured by Pfrimmer-Viggo GMBH & Co KG of Erlangen, Germany may be employed. The Tutoplast ® tissue comes prepackaged in various sizes (length and width). Previously, the material has been primarily used for surgically patching damaged body areas, after being rehydrated in a sterile saline solution.

To form the homograft implant of the present invention, a piece of Tutoplast ® tissue is taken in its purchased dehydrated form and cut into strips of varying shapes and sizes. These strips are then adhesively secured together in a laminar manner by a tissue adhesive. By way of example, Histoacryl ® blue tissue adhesive, which is commercially available from and manufactured by Tri Hawk of Montreal may be used. This particular brand of tissue adhesive, bond virtually instantaneously, thus enabling the surgeon to add layers to the implant as needed during the surgical procedure. Care should be taken when applying the adhesive. If the adhesive is applied too thickly, the heat generated by the adhesive's polymerization process may damage the implant tissue, slowing the healing process.

Figure 2:
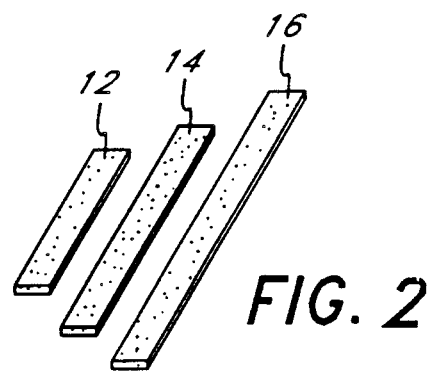
FIG. 2 is an exploded perspective view of an implant made of several strips of thin tissue homograft.
Figure 3:
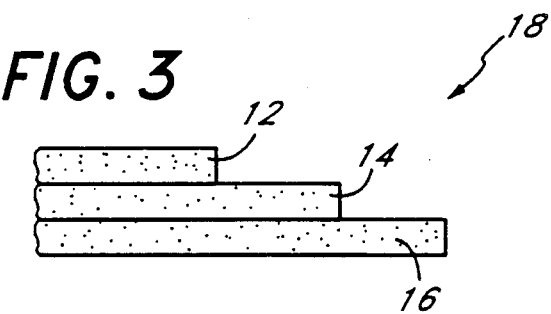
FIG. 3 is a fragmentary side elevational view of the implant illustrated in FIG. 2.

When it is desired to fill a void in a certain area of the body, for example, the nose, the implant tissue is cut into several strips 12, 14 and 16 as shown in FIG. 2. The strips themselves may take on any desired configuration, including but not limited to rectangular, square, round or oval to name a few. The strips are then stacked, as shown in FIG. 3, and adhesively connected together until the implant 18 takes on the desired shape and size sufficient to fill the void. Since the adhesive bonds virtually instantaneously, the formation of the implant may be done in the operating room. In the example illustrated the layers are not of the same size, thus creating a stepped edge configuration.

Figure 4:
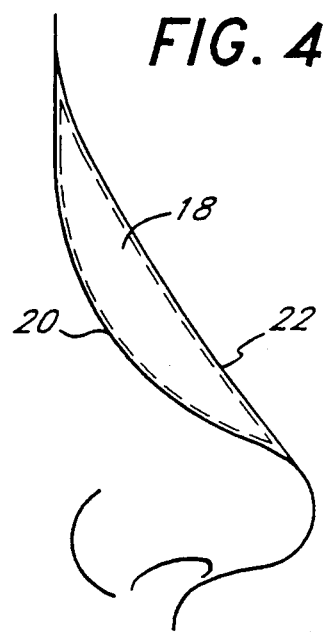
FIG. 4 is a schematic illustration of a human nose, in which the thin tissue homograft implant is implanted.

Once the implant 18 is ready, a small incision is made on the inside of the patient's nostril. The laminar implant is then guided along the nasal septum by the use of forceps, between the nasal cartilage 20 and the dermis 22, as schematically illustrated in FIG. 4. Advantageously, the implant in its dehydrated form is sufficiently stiff so as to facilitate ease of insertion, yet sufficiently flexible so as to be biased toward the nasal cartilage by the outer lying skin. As schematically seen in FIG. 4, the implant 18 has been installed to straighten the bridge of the nose, the implant having been inverted from the position of FIGS. 3 and 4.

Many other modifications and alternative embodiments of the invention will be apparent to those skilled in the art in view of the foregoing description. The described beneath-the-skin procedure may be used for any area of the body where a change of shape or appearance is desired. For example, deep skin creases may be filled. Also, the material may be useful in a "neck lift" that is improving the appearance of neck tissue beneath the jaw. Accordingly, this description is to be construed as illustrative only, and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A method of altering the appearance of a person's physical features, comprising:
   forming an implant of a desired shape of two or more layers of stiff, but formable thin tissue, dehydrated homograft; and
   inserting said implant immediately beneath the person's dermis in a desired location.

2. The method of claim 1, wherein said forming step includes gluing adjacent tissue layers to each other with tissue glue.

3. The method of claim 1, including the step of shaping said implant to conform to the shape of the portion of the person where the implant is to be positioned.

4. The method of claim 1, including cutting said layers in a desired shape from a larger section of said homograft tissue and stacking said layers to form a laminated implant with each layer being glued to the adjacent layers.

5. The method of claim 1, wherein said homograft tissue is made of dura mater.

6. The method of claim 1, wherein said homograft tissue is made of fascia muscle lining.

7. The method of claim 1, wherein said homograft tissue is made of a collagen matrix.

8. The method of claim 1, wherein said inserting step further comprises:
   cutting an opening smaller than the size of said implant;
   endwise inserting said implant through said opening; and
   guiding said implant to said desired location.

9. A method of altering the appearance of a person's nose comprising:
   cutting two or more thin, stiff layers of dehydrated dura mater;
   stacking and gluing the layers together with tissue glue to form an integral implant;
   shaping said implant into the shape necessary to create the desired alteration in appearance;
   forming an incision inside the nasal cavity; and
   inserting said implant through the incision to the desired position in the nose directly beneath the persons dermis.

* * * * *